(12) United States Patent
Brooks

(10) Patent No.: US 10,123,787 B2
(45) Date of Patent: Nov. 13, 2018

(54) COMBINATION INTRODUCER AND STYLET

(71) Applicant: BOSTON MEDICAL CENTER CORPORATION, Boston, MA (US)

(72) Inventor: Jeffrey Brooks, Framingham, MA (US)

(73) Assignee: BOSTON MEDICAL CENTER CORPORATION, Boston, MA (US)

( * ) Notice: Subject to any disclaimer, the term of this patent is extended or adjusted under 35 U.S.C. 154(b) by 459 days.

(21) Appl. No.: 14/774,225

(22) PCT Filed: Feb. 28, 2014

(86) PCT No.: PCT/US2014/019206
§ 371 (c)(1),
(2) Date: Sep. 10, 2015

(87) PCT Pub. No.: WO2014/158669
PCT Pub. Date: Oct. 2, 2014

(65) Prior Publication Data
US 2016/0038126 A1 Feb. 11, 2016

Related U.S. Application Data

(60) Provisional application No. 61/782,162, filed on Mar. 14, 2013.

(51) Int. Cl.
*A61B 6/00* (2006.01)
*A61B 10/02* (2006.01)

(52) U.S. Cl.
CPC .......... *A61B 10/0266* (2013.01); *A61B 6/502* (2013.01); *A61B 10/0275* (2013.01); *A61B 10/0283* (2013.01)

(58) Field of Classification Search
CPC ............ A61B 10/0266; A61B 10/0275; A61B 10/0283; A61B 6/502
See application file for complete search history.

(56) References Cited

U.S. PATENT DOCUMENTS 3,989,033 A 11/1976 Halpern et al.
4,953,558 A 9/1990 Akerfeldt
(Continued)

FOREIGN PATENT DOCUMENTS

EP 1574167 A1 9/2005
EP 2113204 A2 11/2009
(Continued)

OTHER PUBLICATIONS

EnCor Enspire Breast Biopsy System Users Manual (2012).
(Continued)

*Primary Examiner* — Mark Remaly
(74) *Attorney, Agent, or Firm* — Nixon Peabody LLP; Ronald I. Eisenstein; David F. Crosby

(57) ABSTRACT

The elongated substantially tubular introducer extends along a longitudinal axis from a proximal end to a sharpened distal end. The introducer includes at least one side window positioned at a predefined location along the longitudinal axis from a distal tip. The elongated stylet is adapted to be received in a lumen of the tubular introducer to provide structural support for the introducer during insertion and removal. The introducer can be inserted as part of a procedure that includes generating a first image to identify target tissue for biopsy, inserting the introducer into the location of the target tissue based on the first image and then taking a second image, in a substantially transverse or orthogonal direction from the first image in order to ensure proper alignment of target tissue in relation to the at least one side window or to allow for repositioning of the introducer.

21 Claims, 1 Drawing Sheet

(56) References Cited

U.S. PATENT DOCUMENTS

| | | | |
|---|---|---|---|
| 5,620,446 | A | 4/1997 | McNamara et al. |
| 6,773,443 | B2 | 8/2004 | Truwit et al. |
| 7,192,404 | B2 | 3/2007 | Rhad et al. |
| 7,322,940 | B2 | 1/2008 | Burbank et al. |
| 7,711,407 | B2 | 5/2010 | Hughes et al. |
| 7,862,517 | B2 | 1/2011 | Tsonton et al. |
| 2006/0167475 | A1 | 7/2006 | Bischof et al. |
| 2008/0200834 | A1 | 8/2008 | Mark et al. |
| 2008/0275481 | A1 | 11/2008 | Scarpone |
| 2009/0270760 | A1 | 10/2009 | Leimbach et al. |
| 2010/0114031 | A1 | 5/2010 | Jarial et al. |
| 2010/0160818 | A1 | 6/2010 | Haberstich et al. |
| 2011/0125107 | A1 | 5/2011 | Slocum et al. |
| 2013/0030323 | A1 | 1/2013 | Smith |

FOREIGN PATENT DOCUMENTS

| | | |
|---|---|---|
| WO | 03020136 A1 | 3/2003 |
| WO | 2008106583 A1 | 9/2008 |

OTHER PUBLICATIONS

Finesse Ultra Breast Biopsy Probe Users Manual (2011).
Finesse Ultra Introducer Stylet Users Manual (2011).
Vacora Vacuum Assisted Biopsy System Users Manual (2012).
Wilson et al., "Comparison of Large-Core Vacuum-Assisted Breast Biopsy and Excision Systems", Recent Results in Cancer Res. 173:23-41 (2009).

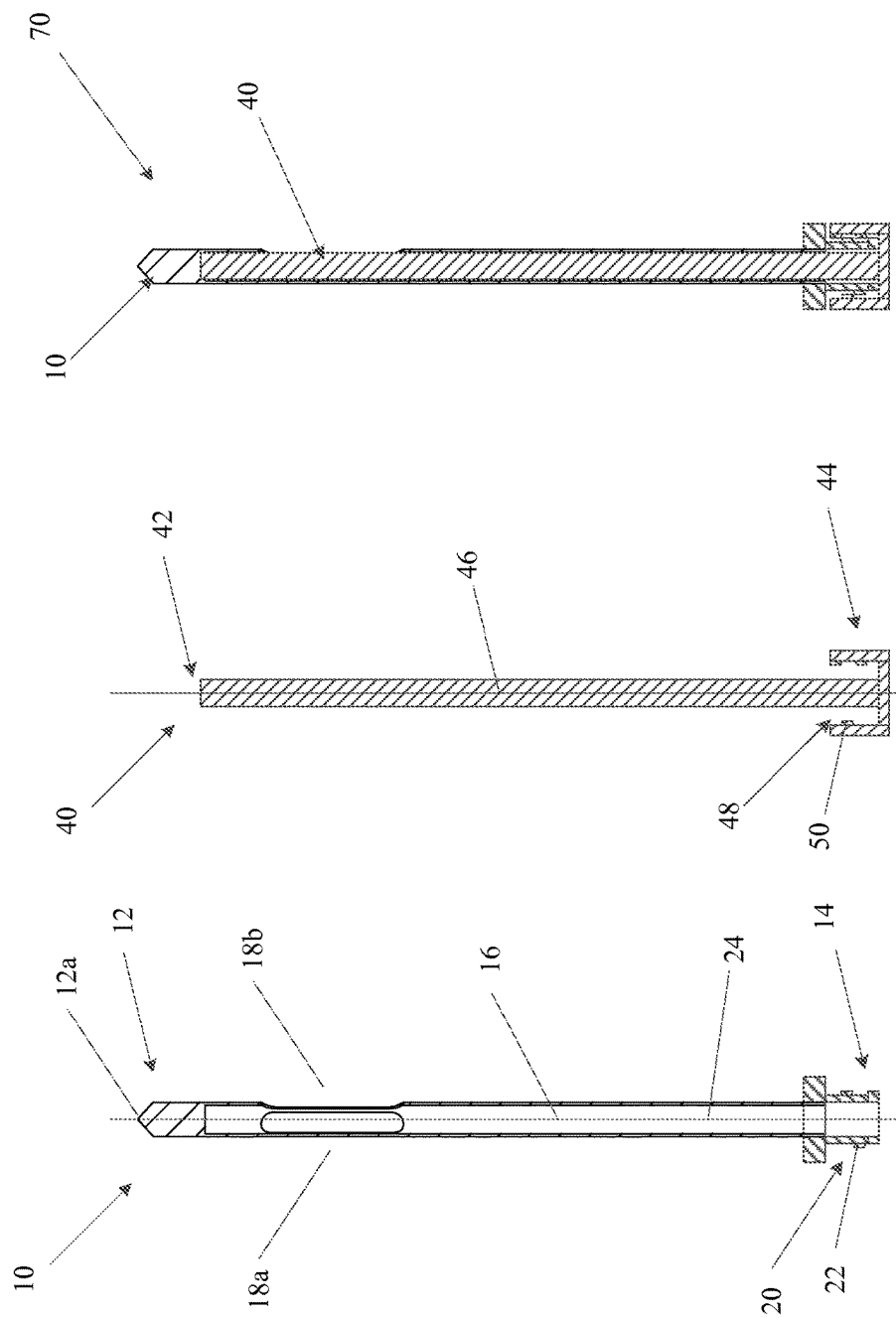

COMBINATION INTRODUCER AND STYLET

CROSS-REFERENCE TO RELATED APPLICATIONS

This application is a 35 U.S.C. § 371 National Phase Entry Application of International Application No. PCT/US2014/019206 filed Feb. 28, 2014, which designates the U.S., and which claims the benefit under 35 U.S.C. § 119(e) of U.S. Provisional Application No. 61/782,162, filed Mar. 14, 2013, the contents of each of which are incorporated herein by reference in their entirety.

STATEMENT REGARDING FEDERALLY SPONSORED RESEARCH

Not Applicable

REFERENCE TO MICROFICHE APPENDIX

Not Applicable.

TECHNICAL FIELD

The present disclosure relates generally to a combination introducer and stylet. More particularly, aspects of the present disclosure relate to a combination introducer and stylet and methods for use in biopsy of tissue, for example, suspicious mammographic findings such as calcifications, masses, asymmetries and architectural distortion in breast tissue.

BACKGROUND

Calcifications in breast tissue can be an indicator of a premalignant condition called ductal carcinoma in situ (DCIS). Thus, the detection of DCIS is a very important part of breast cancer care. In fact, approximately 20% of cancer detected is of the DCIS, pre-invasive type. These cancers can be detected by recognizing certain suspicious patterns of calcifications on screening and diagnostic mammograms. DCIS has been treated similarly as if it was cancer in the United States. Typically, there are two main options for the biopsy of suspicious mammographic findings such as calcifications in breast tissue. The first option involves a needle localization followed by proceeding to the operating room. The second option for a patient is to have a stereotactic biopsy. Stereotactic biopsies can be difficult for both the patient and the physician. There are many limiting factors for stereotactic biopsies and the procedure requires an extra piece of equipment that takes up a significant amount of space. In some cases, this extra equipment can occupy an entire room. Typically, the entire procedure for stereotactic biopsies takes up to 45 minutes or longer in which the patient should remain perfectly still during this time, while her compressed breast falls through a hole in a table. The table does not allow for biopsy of very posterior calcifications and also has a weight limit. Patients will sometimes come for a stereotactic biopsy and then for a variety of reasons the procedure cannot be performed, which wastes both the patient's and physician's time. If a stereotactic biopsy cannot be performed, a patient will need surgery in the operating room for further evaluation.

There is still a need for improved equipment and biopsy methods of tissue, including calcifications and other suspicious mammographic findings in breast tissue, that overcomes the disadvantages of existing methods.

SUMMARY

A combination includes an introducer and stylet. The elongated substantially tubular introducer extends along a longitudinal axis from a proximal end to a sharpened distal end. The introducer includes at least one window positioned at a predefined location along the longitudinal axis from a distal tip. The introducer includes a radio-opaque material. The elongated stylet extends along a longitudinal axis from a proximal end to a distal end. The stylet is adapted to be received in a lumen of the tubular introducer. The proximal end of the introducer is adapted to releasably engage with the proximal end of the stylet when the stylet is placed in the lumen of the introducer.

A method of taking a core biopsy includes providing an introducer being an elongated substantially hollow member extending along a longitudinal axis from a proximal end to a sharpened distal end. The introducer includes at least one window spaced from a distal tip. The introducer includes a radio-opaque material. A stylet extending along a longitudinal axis from a proximal end to a distal end is provided. The stylet is received in a lumen of the tubular introducer. The introducer and stylet is inserted into tissue. The stylet is disengaged from the introducer. A biopsy of the tissue is taken via the at least one window of the introducer.

The method can also be performed in conjunction with one or more imaging technologies to improve positioning of the introducer to take the biopsy. These imaging technologies can include X-ray, ultrasound, CT scanning, and MRI. In accordance with some embodiments of the invention, the area to be biopsied can be imaged in one direction to identify suspect tissue, the introducer and stylet can be inserted into the area of suspect tissue and then a second image can be taken along an axis perpendicular to the axis of the introducer. Because the introducer includes one or more radio-opaque portions (e.g. marking the extent of the windows), the location of the windows of the introducer and the suspect tissue can be identified on the second image and the position of the windows of the introducer can be adjusted based on the distance shown in the second image. For example, if the suspect tissue is 5 mm proximal to the windows, the depth of the introducer can be adjusted 5 mm or more so that the suspect tissue is aligned with the windows.

An introducer for taking a biopsy includes an elongated substantially tubular member extending along a longitudinal axis from a proximal end to a sharpened distal end. The introducer includes at least one window spaced from a distal tip. The introducer includes a radio-opaque material. The introducer further includes a mechanism for opening and closing the window.

The above summary is not intended to represent each embodiment or every aspect of the present disclosure. Rather, the summary merely provides an exemplification of some of the novel features presented herein. The above features and advantages, and other features and advantages of the present disclosure, will be readily apparent from the following detailed description of exemplary embodiments and modes for carrying out the present invention when taken in connection with the accompanying drawings and the appended claims.

BRIEF DESCRIPTION OF THE DRAWINGS

FIG. 1 is a plan view of an outer portion of an introducer according to one embodiment of the present disclosure.

FIG. 2 is a plan view of a stylet according to one embodiment of the present disclosure.

FIG. 3 is a combination of the introducer of FIG. 1 and the stylet of FIG. 2.

While aspects of this disclosure are susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

This invention is susceptible of embodiments in many different forms. Some of these are shown in the drawings and will herein be described in detail representative embodiments of the invention with the understanding that the present disclosure is to be considered as an exemplification of the principles of the invention and is not intended to limit the broad aspects of the invention to the embodiments illustrated.

The introducer of the present invention assists in taking biopsies of tissue. The introducer of the present invention includes at least one side opening or window positioned along the axial length of introducer and in some embodiments, at or near its distal end. The at least one window can be located on the side of the introducer and tissue can enter the introducer though the window. By using the side of the introducer, the biopsy device can be rotated 360 degrees within the introducer to take biopsies at different positions from the original insertion along the circumference of the introducer. In addition, the introducer can include marker elements, such as radio-opaque portions, that enable the introducer to be visible using well known imaging technologies, such as X-rays and ultrasound, to enable the introducer to be more closely positioned to the suspect tissue to be biopsied.

A non-limiting example of an introducer is shown in FIG. 1. FIG. 1 depicts an introducer 10 that is an elongated substantially tubular member extending along a longitudinal axis 16. The introducer 10 includes a distal end 12 and a proximal end 14. The distal end 12 includes a sharpened portion (e.g., a cutting needle tip) that assists in cutting tissue during insertion of the introducer into the tissue. The proximal end 14 provides access to the lumen to receive a stylet and a flange to enable it to be secured to a stylet.

FIG. 1 specifically shows an implementation that includes a plurality of windows 18a, 18b spaced from a distal tip 12a. It is contemplated that the plurality of windows can include exactly 1, 2 or 3 windows or even more windows. The plurality of windows 18a, 18b can be circumferentially spaced around the introducer and positioned along the longitudinal axis at a predefined distance from the distal tip. In another implementation, the at least one widow can be directly adjacent to the distal tip. In accordance with one embodiment as shown in FIG. 1, the windows can be as large as possible extending circumferentially around the introducer providing the minimal amount material between adjacent windows to provide structural stability. In some embodiments of the invention, the introducer can rely on the stylet inserted into the introducer and extending beyond the windows to provide structural support. The shape and size of the at least one window can differ from that shown in FIG. 1. The at least one window can be sized to receive a specific amount of tissue during the biopsy. By rotating the at least one window 18a, 18b, or by rotating the biopsy device within the introducer, a circumferential biopsy can be taken without repositioning the introducer 10. The at least one window allows for more accurate targeting of the calcifications and with less steps for confirming accurate positioning of the introducer. The biopsy occurs through the side of the introducer 10 and not at a distal tip 12a of the introducer 10.

The introducer 10 can include marker elements that include a radio-opaque material to assist in positioning the introducer with respect to the tissue (e.g., suspicious mammographic findings such as calcifications, masses, asymmetries, and architectural distortions). The marker elements can be used to identify the location of at least one portion of the introducer in an image of tissue to be biopsied. The radio-opaque material of the introducer can be any material that will appear in an image of tissue taken below the skin. For example, where the image is taken using X-rays, the marker elements can be radio-opaque materials, such as, a metal. Non-limiting examples of metals that can be used in forming the introducer include, but are not limited to, stainless steels, titanium, alloys and combinations thereof. Typically, the distal end 12 and the longitudinal axis 16 of the introducer 10 are formed of radio-opaque material. The longitudinal axis 16 may vary in length to assist in the positioning into the tissue without proceeding to an unnecessary depth. In some embodiments of the invention, the marker elements can indicate the position and extent of the windows, allowing a physician to determine from an image, distance that the introducer needs to be adjusted, either by inserting it deeper into the tissue or removing it outward to align the windows with the suspect tissue to be biopsied.

As will be discussed in detail below, the proximal end of the introducer can be adapted to releasably engage with a proximal end of a stylet when the stylet is placed in the lumen of the introducer. One non-limiting method of releasably engaging the proximal end of the introducer and the proximal end of the elongated stylet including a fastening mechanism such as a screwing mechanism.

Referring still to FIG. 1, the proximal end 14 of the introducer 10 includes a fastening mechanism (e.g., screwing mechanism 20). The screwing mechanism 20 includes exterior threads 22. The introducer and the stylet when screwed together or fastened together improve the strength and stability during the insertion process as compared to using the introducer alone.

The proximal end 14 of the introducer 10 can be made of a radiolucent material. Non-limiting examples of radiolucent materials include polymeric materials. Non-limiting examples of polymeric material that may be used in forming the proximal end of the introducer include, but are not limited to, thermoplastics. It is contemplated that the proximal end may be made of other materials including radio-opaque materials.

The introducer and, more specifically, the outer diameter of the introducer generally can be less than about 8 mm and typically has a diameter less than about 7 mm. The introducer can be a specialized introducer. The lumen of the introducer can generally be less than 7 mm and typically has a diameter of about 5 mm.

A stylet assists in providing structural support to the introducer during the insertion process. The introducer typically does not have the desired structural strength because of the formed window. The stylet can also obstruct the at least one window of the introducer during the insertion to prevent tissue from entering the introducer during insertion. The stylet may be a hollow member or may be a solid member.

A hollow stylet may be referred to as an aspiration needle. If the stylet is a hollow member, it can be used to selectively expose tissue while still being within the introducer. If the stylet is a solid member, it is typically removed so that tissue can be more easily accessed for biopsy. Alternatively, the hollow introducer can be used directly as an aspiration needle.

A non-limiting example of a stylet 40 is shown in FIG. 2. FIG. 2 depicts the elongated stylet 40 extending along a longitudinal axis 46 from a proximal end 44 to a distal end 42. The stylet 40 can be adapted to be placed in a lumen 24 of the hollow introducer 10 (see FIG. 1). The combination 70 of the introducer 10 and the stylet 40 is shown in FIG. 3 in a fully inserted or engaged position. FIG. 3 also depicts the stylet 40 extending beyond the windows of introducer 10 and against the distal aspect of the introducer 10 when in a fully inserted and secured position.

Referring back to FIG. 2, the distal end 42 of the stylet 40 can have flat or angled distal end. The distal end may form other shapes, but it is not necessary to be pointed since the distal end does of the stylet does not cut tissue. The proximal end 44 of the stylet 40 includes a fastening or screwing mechanism. The proximal end 44 includes a screwing mechanism 48 having internal threads 50 that engage the exterior threads 24 of the introducer 10 as part of the fastening mechanism 22.

It is contemplated that the introducer and the stylet may be releasably engaged by other methods than the screwing mechanism shown in FIGS. 1-3. For example, the introducer and stylet may be releasably engaged by mechanisms including a hook or a nob on the stylet that engages with a notch on the introducer. The hook, knob or screwing mechanism can also be used to engage with a biopsy clip deployment device.

In one implementation, the stylet may be made of radiolucent material. The radiolucent material of the stylet is typically a polymeric material. Non-limiting examples of polymeric materials that can be used in forming the stylet include, but are not limited to, thermoplastics. The stylet may be made of radio-opaque material such as a metallic material.

According to one method, an vacuum-assisted core biopsy can be taken after positioning of the introducer with the stylet engaged. The introducer is an elongated substantially tubular hollow member. The introducer can have an elongated body that extends along a longitudinal axis from a proximal end to a sharpened distal end. The introducer provides at least one window positioned at a predefined distance from a distal tip and includes a radio-opaque material that can act as reference markers for the window location when viewed in an X-ray or other image. The stylet has an elongated body that extends along a longitudinal axis from a proximal end to a distal end. The stylet can be inserted into an interior lumen of the introducer. The introducer and stylet, their assembled configuration can be inserted into the tissue area to be biopsied. The proximal end of the introducer can be disengaged from the proximal end of the stylet and the stylet can be partially or completely withdrawn, exposing the tissue to be biopsied. A biopsy can be taken of the tissue via the at least one window of the introducer.

The introducer after being inserted into the tissue can be rotated in either a clockwise or counterclockwise direction to reposition the window and biopsy tissue around the periphery of the introducer. The rotational movement of the introducer is easier when the stylet is fully engaged with the introducer. The introducer with circumferential windows could also be stationary within the tissue and allow the biopsy device to rotate 360 degrees to ensure adequate sampling of small targets within the tissue. The introducer, however, can be rotated with the stylet being inserted therein. The ability to rotate the introducer is especially advantageous when the area to be biopsied is small. The benefit from the introducer is to allow the biopsy device to rotate which expands the biopsied area to be of a 3-dimensional nature as opposed to being 2-dimensional. This benefit would also allow for quicker biopsy of larger volume of tissue without the need to reposition the introducer.

During the process, the disengagement of the stylet with respect to the introducer can be a partial disengagement such that the stylet is removed from a fully inserted position (FIG. 3) to a retracted position where the tissue can enter through the window of the introducer. The disengagement of the introducer can be fully disengaged such that the stylet does not contact the introducer.

The tissue can be removed from the introducer by several methods. One non-limiting example is to use a vacuum-assisted device that includes a filter or membrane that catches the biopsied tissue.

One example of tissue that can be biopsied using the combined introducer and stylet is breast tissue. More specifically, the calcifications (e.g., microcalcifications) in the breast tissue may be biopsied using the combined introducer and stylet. To biopsy these calcifications, the location in three dimensional space within the breast tissue needs to be known. Because these microcalcifications in breast tissue are small, the introducer of the present invention is advantageous because it allows for precise localization and visualization of the microcalcifications though the at least one window and because it allows circumferential tissue biopsy without the need to adjust or reinsert the introducer.

The biopsies of calcifications (and/or other suspicious mammographic and radiographic findings in tissue) can be performed using 2-dimensional mammography. In accordance with one embodiment, a first image (e.g., an X-ray) of the breast can be taken to identify the location of calcifications. Using this first image, the introducer and stylet can be inserted into the location where the calcifications were identified. After the introducer and stylet are inserted, a second image (e.g. an X-ray or ultrasound) taken along an axis perpendicular to the longitudinal axis of the introducer can be taken to assess the position of the windows relative to the calcifications enabling the caregiver to adjust, as necessary, the introducer into or out of the tissue to align the windows with the calcifications to be biopsied. After the introducer is aligned, the stylet can be removed and a conventional biopsy device or vacuum assisted core biopsy device can be inserted into the lumen of the introducer up to the area of the windows and one or more biopsies can be taken. In accordance with some embodiments of the invention, the biopsy device can include a side aspiration window that aligns with the windows in the introducer and location of the biopsy can be adjusted by rotating the biopsy device to orient the side aspiration window to take the biopsy in the desired location. Where the windows of the introducer do not extend all the way around the circumference of the introducer, the introducer can also be rotated to biopsy different locations around the distal end. The introducer and the biopsy device can include marks or indicators that provide the user with an indication of the position of the windows of their respective devices. Utilizing the biopsy device in the procedure according to the invention provides for substantially shorter procedure that is easier for both the patient and the caregiver. The method can also include X-ray visualization. It is necessary that the second image be taken along an axis perpendicular to the longitudinal axis of the introducer, the second image can be taken at substantially any angle, however more complex calculations would need to be made to determine the proper adjustment of the insertion depth of the introducer to align it with the target tissue.

A biopsy using the inventive methods can be obtained in less than 30 minutes and typically in about 20-25 minutes. This procedure can be performed with the patient sitting in a chair instead of lying on a table and without any additional add-on pieces of equipment for the standard 2 dimensional mammogram machine.

EXAMPLES

Prototypes of this device were made to work with the Hologic ATEC biopsy device and the Bard Encor Ultra with sizes ranging from 7 to 12 gauge in diameter. A model using turkey meat injected with a suspension of crushed eggshells simulated a breast with microcalcifications for early experiments. 30 trials were performed with 3 different users who had 3 different levels of experience, attending radiologist, radiology fellow and radiology resident. On each of the 30 attempts, there was successful retrieval of crushed eggshells using the specialized introducer with at least one window using the method for biopsy of calcifications described herein.

There are many benefits to the use of the device and method according to the invention. These benefits include decreasing costs by eliminating the need for a stereotactic biopsy system which can cost as much as $250,000 or more and needs to be replaced every 10-12 years. These expensive systems need to be housed in a large room and are not used often (e.g., on average twice per week over a two year period at one major medical center). The methods according to the present invention can be performed using standard 2D mammography machines which are readily available. No expensive additional equipment would be necessary. This procedure would increase the availability of this procedure to patients in rural and underserved areas.

This procedure would obviate the need for some patients to have an open surgery. At a major medical center from January 2011 to December 2012, there were 288 recommendations for biopsy, mostly for calcifications, for which the only option was either stereotactic biopsy or open surgery. Of these cases, 84 biopsies either failed an attempt with stereotactic biopsy or were recommended to go directly to excisional biopsy with an open surgery because of technical factors. Most if not all of these 84 cases could have been spared an open surgery which involves increased morbidity and mortality if this specialized introducer was available. This method/procedure is physically easier and more comfortable for patients to endure and shorter in duration.

The methods of present invention are advantageous in that there are lower complications and less time lost for failed procedures that can happen as compared with prior art stereotactic biopsies. These inventive methods also decrease the number of patients who need to go to the operating room for excisional biopsy of calcifications. These inventive methods also result in less radiation to the patient and less overall time needed to perform the biopsy of calcifications. Also, by reducing repositioning of the introducer, less radiation is exposed to the patient. Thus, in summary, the inventive methods makes patients care improved and safer, while decreasing the total health care cost for biopsy of calcifications in the tissue.

In another embodiment, the stylet can also form a side window therein. In this embodiment, the elongated member of the stylet can include at least one side window. This side window of the stylet can be positioned to align with the at least one window of the introducer when the stylet is inserted into the introducer. An opening for taking a biopsy can be formed by aligning the respecting windows of the introducer and the stylet. The opening can be closed, such as for insertion, when a solid portion of the stylet aligns with the window of the introducer. The windows can be aligned by rotating the introducer and the stylet with respect to each other. A marker indicating the position of the window can be provided at the proximal end of the introducer and a marker indicating the position of the window can be provided at the proximal end of the stylet so that the windows can be aligned by aligning the markers.

In yet another embodiment, an introducer can include a mechanism to open and close the at least one window after the introducer has been inserted. In this embodiment, the stylet may not be needed if the introducer has sufficient strength for the insertion process.

In yet a further embodiment, the stylet can also be hollow, which allows for a biopsy device to be inserted through the combined hollow stylet and introducer. After adequate positioning of the biopsy device, the hollow stylet can then be retracted so that the at least one window is exposed allowing for biopsy through the at least one window. This may be advantageous in that the hollow stylet may prevent or inhibit excessive tissue from infiltrating the device through the at least one window during insertion.

While many embodiments and modes for carrying out the present invention have been described in detail above, those familiar with the art to which this invention relates will recognize various alternative designs and embodiments for practicing the invention within the scope of the appended claims.

What is claimed is:

1. A combination introducer and stylet, the combination comprising:

an elongated substantially tubular introducer extending along a longitudinal axis from a proximal end to a sharpened distal end, the introducer including at least one window positioned at a predefined location along the longitudinal axis from a distal tip, the introducer including a lumen adapted to receive a biopsy device and wherein the lumen extends from the proximal end to the distal end of the introducer such that the biopsy device can access tissue through the at least one window, and wherein the introducer includes one or more radio-opaque portions marking an extent of the at least one window; and an elongated stylet extending along a longitudinal axis from a proximal end to a distal end, the stylet being adapted to be received in the lumen of the tubular introducer, wherein the proximal end of the introducer is adapted to releasably engage with the proximal end of the stylet when the stylet is placed in the lumen of the introducer and wherein when the proximal end of the stylet is engaged with the proximal end of the stylet the distal end of the stylet extends into the distal end of the introducer to support and stabilize the introducer during insertion.

2. The combination introducer and stylet of claim 1, wherein the radio-opaque material of the introducer is a metal.

3. The combination introducer and stylet of claim 2, wherein the proximal end of the introducer comprises polymeric material.

4. The combination introducer and stylet of claim 1, wherein the stylet is radiolucent.

5. The combination introducer and stylet of claim 4, wherein the stylet comprises polymeric material.

6. The combination introducer and stylet of claim 1, wherein the introducer includes a plurality of windows spaced from the distal end.

7. The combination introducer and stylet of claim 1, wherein the introducer includes a plurality of windows circumferentially spaced around the introducer and located at a predefined position along the longitudinal axis from the distal end.

8. The combination introducer and stylet of claim 7, wherein the introducer includes at least three windows circumferentially spaced from the distal end.

9. The combination introducer and stylet of claim 1, wherein the stylet is hollow.

10. The combination introducer and stylet of claim 1, wherein the stylet is solid.

11. The combination introducer and stylet of claim 1, wherein the proximal end of the introducer releasably engages the proximal end of the stylet via a screwing mechanism.

12. A method of taking a core biopsy, the method comprising the acts of:
providing an introducer being an elongated substantially hollow member extending along a longitudinal axis from a proximal end to a sharpened distal end, the introducer including at least one window spaced from a distal tip, the introducer including a radio-opaque material;
providing a stylet extending along a longitudinal axis from a proximal end to a distal end, the stylet being received in a lumen of the tubular introducer such that the distal end of the stylet extends into the distal end of the introducer to support and stabilize the introducer during insertion,
inserting the introducer and stylet into tissue;
disengaging the stylet from the introducer;
inserting a biopsy device into the introducer; and
taking a biopsy of the tissue via the at least one window of the introducer.

13. The method of claim 12, wherein the combined introducer and stylet is inserted into breast tissue.

14. The method of claim 13, wherein the biopsy is directed to suspicious mammographic findings in the breast tissue.

15. The method of claim 14 wherein the suspicious mammographic findings include at least one of calcifications, asymmetries, masses or architectural distortions.

16. The method of claim 12 further including the act of using 2-dimensional mammography to guide the biopsy.

17. The method of claim 12 further including the act of X-ray imaging.

18. The method of claim 12, wherein the introducer allows biopsy device rotation after being inserted into the tissue.

19. The method of claim 12, wherein the stylet is partially removed from the introducer such that the distal end of the stylet is exposed to the at least one window of the introducer such that one or more biopsies can be performed via the at least one window of the introducer.

20. An introducer for taking a biopsy, the introducer comprising an elongated substantially tubular member extending along a longitudinal axis from a proximal end to a sharpened distal end, the introducer including at least one window spaced from a distal tip, the introducer including a lumen adapted to receive a biopsy device and wherein the lumen extends from the proximal end to the distal end of the tubular member such that the biopsy device can access tissue through the at least one window, and wherein the introducer includes one or more radio-opaque portions marking an extent of the at least one window, the introducer further including a mechanism for opening and closing the at least one window.

21. A method of taking a biopsy comprising:
generating a first image of an area of tissue to be biopsied, the image indicating suspect tissue in at least one location;
inserting a hollow introducer into the suspect tissue at the at least one location, the hollow introducer extending along a longitudinal axis from a proximal end to a distal end and including at least one side window at predefined distance from the distal end;
generating a second image of the suspect tissue showing at least a portion of the introducer extending along the longitudinal axis in relation to the suspect tissue;
adjusting the insertion of the introducer to align the at least one side window with the suspect tissue; and
aspirating some of the suspect tissue through the at least one side window.

* * * * *